(12) United States Patent
Camden et al.

(10) Patent No.: US 6,225,307 B1
(45) Date of Patent: May 1, 2001

(54) VIRAL TREATMENT

(75) Inventors: James Berger Camden, West Chester; Joseph Herman Gardner, Cincinnati; David Thomas Stanton, Hamilton, all of OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/538,005

(22) Filed: Mar. 29, 2000

Related U.S. Application Data

(63) Continuation-in-part of application No. 09/281,893, filed on Mar. 31, 1999, now abandoned.

(51) Int. Cl.[7] .................................................... A61K 31/55
(52) U.S. Cl. ...................................................... 514/212.03
(58) Field of Search ................................ 514/212, 212.03

(56) References Cited

U.S. PATENT DOCUMENTS

| 4,724,232 | * | 2/1988 | Rideout et al. ....................... 514/50 |
| 5,114,951 |   | 5/1992 | King ..................................... 514/290 |
| 5,656,639 | * | 8/1997 | Edmonds-Alt et al. ............. 514/305 |

FOREIGN PATENT DOCUMENTS

| 2 056 439 |   | 3/1981 | (GB) . |
| 2056439   | * | 3/1981 | (GB) ........................... C07D/223/04 |
| WO 98/45271 |  | 10/1998 | (WO) . |

OTHER PUBLICATIONS

Shepherd, et al., J. Chem Soc. Perkin Trans I, 1987, pp. 2153–2155.
Hilpert, WO 9845271 (Abstract), 1998.*
* cited by examiner

*Primary Examiner*—Russell Travers
(74) *Attorney, Agent, or Firm*—Rose Ann Dabek; Steven W. Miller

(57) ABSTRACT

A pharmaceutical composition that inhibits or slows the growth of viruses in animals, particularly in mammals, is disclosed. This same composition is can be used to treat viral infections, particularly HIV. The composition comprises from about 10 mg to about 10000 mg of a carbamic acid ester derivative of the formula:

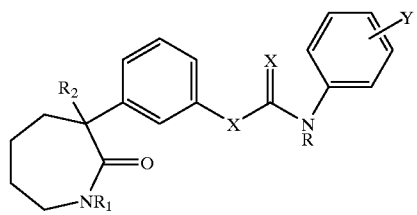

wherein X is independently oxygen or sulfur, R is selected from the group consisting of hydrogen and alkyl having from 1 to 4 carbon atoms, $R_1$ is selected from the group consisting of hydrogen and alkyl having from 1 to 4 carbon atoms, wherein $R_2$ is independently selected from the group consisting of hydrogen and alkyl having from 1 to 4 carbon atoms, and wherein Y is selected from the group consisting of hydrogen, chloro, fluoro, bromo, hydroxy, oxychloro and sulfhydryl or pharmaceutical addition salt or prodrug thereof. The most preferred compound is (4-chlorophenyl)-carbamic acid, 3-(hexahydro-3-ethyl-1-methyl-2-oxo-1H-azepin-3-yl) 2 phenyl ester.

43 Claims, No Drawings

VIRAL TREATMENT

This application is a continuation in part of application of J. B. Camden, Ser. No. 09/281,893, filed Mar. 31, 1999 now abandoned.

TECHNICAL FIELD

This invention relates to certain carbamic acid esters that are effective against viruses and can be used to treat viral infections in animals. The preferred compound is (4-chlorophenyl)-carbamic acid, 3-(hexahydro-3-ethyl-1-methyl-2-oxo-1H-azepin-3-yl) 2 phenyl ester. The composition can contain one or more of the carbamic acid esters, its pharmaceutical addition salt or prodrugs thereof.

BACKGROUND OF THE INVENTION

HIV and other viral infections, such as hepatitis, are a few of the leading causes of death. HIV is the virus known to cause acquired immunodeficiency syndrome (AIDS) in humans. HIV is a disease in which a virus is replicated in the body or in host cells. The virus attacks the body's immune system.

Several drugs have been approved for treatment of this devastating disease, including azidovudine (AZT), didanosine (dideoxyinosine, ddI), d4T, zalcitabine (dideoxycytosine, ddC), nevirapine, lamivudine (epivir, 3TC), saquinavir (Invirase), ritonavir (Norvir), indinavir (Crixivan), and delavirdine (Rescriptor). See M. I. Johnston & D. F. Hoth, *Science,* 260 (5112), 1286–1293 (1993) and D. D. Richman, *Science,* 272 (5270), 1886–1888 (1996). An AIDS vaccine (Salk's vaccine) has been tested and several proteins which are chemokines from CD8 have been discovered to act as HIV suppressors. In addition to the above synthetic nucleoside analogs, proteins, and antibodies, several plants and substances derived from plants have been found to have in vitro anti-HIV activity. However, HIV virus is not easily destroyed nor is there a good mechanism for keeping the host cells from replicating the virus.

Thus, medical professionals continue to search for drugs that can prevent HIV infections, treat HIV carriers to prevent their disease from progressing to full-blown deadly AIDS, and to treat the AIDS patient.

Herpes simplex virus (HSV) types 1 and 2 are persistent viruses that commonly infect humans; they cause a variety of troubling human diseases. HSV type 1 causes oral "fever blisters" (recurrent herpes labialis), and HSV type 2 causes genital herpes, which has become a major venereal disease in many parts of the world. No fully satisfactory treatment for genital herpes currently exists. In addition, although it is uncommon, HSV can also cause encephalitis, a life-threatening infection of the brain. (*The Merck Manual,* Holvey, Ed., 1972; Whitley, Herpes Simplex Viruses, In: *Virology,* 2nd Ed., Raven Press (1990)). A most serious HSV-caused disorder is dendritic keratitis, an eye infection that produces a branched lesion of the cornea, which can in turn lead to permanent scarring and loss of vision. Ocular infections with HSV are a major cause of blindness. HSV is also a virus which is difficult, if not impossible to cure.

Hepatitis is a disease of the human liver. It is manifested with inflammation of the liver and is usually caused by viral infections and sometimes from toxic agents. Hepatitis may progress to liver cirrhosis, liver cancer, and eventually death. Several viruses such as hepatitis A, B, C, D, E and G are known to cause various types of viral hepatitis. Among them, HBV and HCV are the most serious. HBV is a DNA virus with avirion size of 42 nm. HCV is a RNA virus with a virion size of 30–60 nm. See D. S. Chen, *J. Formos. Med. Assoc.,* 95 (1), 6–12 (1996).

Hepatitis C infects 4 to 5 times the number of people infected with HIV. Hepatitis C is difficult to treat and it is estimated that there are 500 million people infected with it worldwide (about 15 time those infected with HIV). No effective immunization is currently available, and hepatitis C can only be controlled by other preventive measures such as improvement in hygiene and sanitary conditions and interrupting the route of transmission. At present, the only acceptable treatment for chronic hepatitis C is interferon which requires at least six (6) months of treatment and or ribavarin which can inhibit viral replication in infected cells and also improve liver function in some people. Treatment with interferon with or without Ribavirin however has limited long term efficacy with a response rate about 25%.

Hepatitis B virus infection lead to a wide spectrum of liver injury. Moreover, chronic hepatitis B infection has been linked to the subsequent development of hepatocellular carcinoma, a major cause of death. Current prevention of HBV infection is a hepatitis B vaccination which is safe and effective. However, vaccination is not effective in treating those already infected (i.e., carriers and patients). Many drugs have been used in treating chronic hepatitis B and none have been proven to be effective, except interferon.

Treatment of HCV and HBV with interferon has limited success and has frequently been associated with adverse side effects such as fatigue, fever, chills, headache, myalgias, arthralgias, mild alopecia, psychiatric effects and associated disorders, autoimmune phenomena and associated disorders and thyroid dysfunction.

Because the interferon therapy has limited efficacy and frequent adverse effects, a more effective regimen is needed.

In the present invention it has been discovered that the compounds described above are useful for the treatment of hepatitis C virus, hepatitis B virus, herpes simplex and the treatment of HIV infection and other viral infections.

SUMMARY OF THE INVENTION

A pharmaceutical composition for treatment of animals, and in particular, warm blooded animals, including humans, comprising a pharmaceutical carrier and an effective amount of an aryl carbamic acid ester having the following formula:

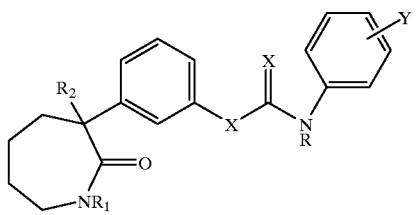

wherein X is independently oxygen or sulfur, R is selected from the group consisting of hydrogen and alkyl having from 1 to 4 carbon atoms, $R_1$ is selected from the group consisting of hydrogen and alkyl having from 1 to 4 carbon atoms, wherein $R_2$ is independently selected from the group consisting of hydrogen and alkyl having from 1 to 4 carbon atoms, and wherein Y is selected from the group consisting of hydrogen, chloro, fluoro, bromo, hydroxy and sulfhydryl or a pharmaceutical addition salts or prodrug thereof.

The preferred compound is (4-chlorophenyl)-carbamic acid, 3-(hexahydro-3-ethyl-1-methyl-2-oxo-1H-azepin-3-yl) 2 phenyl ester; wherein X is oxygen, Y is chloro, R is hydrogen, $R_2$ is ethyl and $R_1$ is methyl.

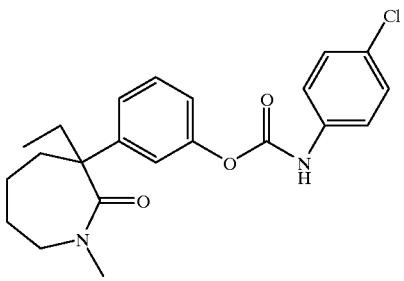

The compositions can be used in a method of treating HIV, in particular chronic HIV, and other viral infections. The drug can be given daily in one or more doses and from 1 to 4 times a week.

The compositions can be used in conjunction with other treatments for the viral infections.

DETAILED DESCRIPTION OF THE INVENTION

A. Definitions:

As used herein "alkyl" includes straight, branched chain and cyclic alkanes.

As used herein "aryl" includes phenyl or phenyl derivatives, for example, chlorophenyl, fluorophenyl, or methylphenyl.

As used herein, the term "safe and effective amount" refers to the quantity of a component which is sufficient to yield a desired therapeutic response without undue adverse side effects (such as toxicity, irritation, or allergic response) commensurate with a reasonable benefit/risk ratio when used in the manner of this invention.

As used herein, the term "therapeutically effective amount" is meant an amount of a compound of the present invention effective to yield the desired therapeutic response. For example to inhibit HIV infection or treat the symptoms of infection in a host or an amount effective to treat hepatitis. The specific safe and effective amount or therapeutically effective amount will, obviously, vary with such factors as the particular condition being treated, the physical condition of the patient, the type of mammal being treated, the duration of the treatment, the nature of concurrent therapy (if any), and the specific formulations employed and the structure of the compounds or its derivatives.

As used herein, a "pharmaceutical addition salts" is salt of the aryl carbamic acid ester derivative which is modified by making acid or base salts of the compound. Examples of pharmaceutically acceptable salts include, but are not limited to, mineral or organic acid salts of basic residues such as amines, alkali or organic salts of acidic residues such as carboxylic acids. Preferably the salts are made using an organic or inorganic acid. These preferred acid addition salts are chlorides, bromides, sulfates, nitrates, phosphates, sulfonates, formates, tartrates, maleates, malates, citrates, benzoates, salicylates, ascorbates, and the like.

As used herein, a "pharmaceutical carrier" is a pharmaceutically acceptable solvent, suspending agent or vehicle for delivering the anti-viral agent to the animal or human. The carrier can be liquid or solid and is selected with the planned manner of administration in mind.

As used herein, the terms "anti-viral compound" means an aryl carbamic acid ester or pharmaceutically acceptable salt thereof or a prodrug of the carbamic acid ester.

As used herein, the term "carbamic acid ester derivative" or "aryl carbamic acid ester" are compounds having the formula:

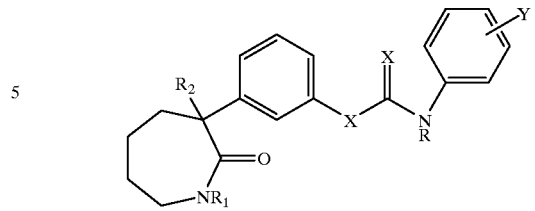

wherein X is independently oxygen or sulfur, R is selected from the group consisting of hydrogen and alkyl having from 1 to 4 carbon atoms, $R_1$ is selected from the group consisting of hydrogen and alkyl having from 1 to 4 carbon atoms, wherein $R_2$ is independently selected from the group consisting of hydrogen and all having from 1 to 4 carbon atoms, and wherein Y is selected from the group consisting of hydrogen, chloro, fluoro, bromo, hydroxy, oxychloro, and sulfhydryl or a pharmaceutical addition salts or prodrug thereof "Prodrugs" are considered to be any covalently bonded carriers which release the active parent drug according to the formula of derivatives described above in vivo when such prodrug is administered to a mammalian subject. Prodrugs of the aryl carbamic acid ester are prepared by modifying functional groups present in the compounds in such a way that the modifications are cleaved, either in routine manipulation or in vivo, to the parent compounds. Prodrugs include compounds wherein free hydroxyl, sulfhydryl, or amine groups are bonded to any group that, when administered to a mammalian subject, cleaves to form a free hydroxyl, amino, or sulfhydryl group, respectively. Examples of prodrugs include, but are not limited to, acetate, formate, or benzoate derivatives of alcohol and amine functional groups in the carbamic acid ester derivatives; phosphate esters, dimethylglycine esters, aminoalkylbenzyl esters, aminoalkyl esters and carboxyalkyl esters of alcohol and phenol functional groups in the carbamic acid ester derivatives; and the like.

As used herein "viruses" includes viruses which infect animals or mammals, including humans. Viruses includes retrovirus, HIV, influenza, polio viruses, herpes simplex, hepatitis B, C and other viral strains of hepatitis, Kaposi's sarcoma, rhinoviruses, and the like.

As used herein "combination therapy" means that the patient in need of the drug is treated or given another drug for the disease in conjunction with the carbamic acid ester derivatives. This combination therapy can be sequential therapy where the patient is treated first with one drug and then the other or the two drugs are given simultaneously.

As used herein, a "pharmaceutically acceptable" component is one that is suitable for use with humans and/or animals without undue adverse side effects (such as toxicity, irritation, and allergic response) commensurate with a reasonable benefit/risk ratio.

As used herein, a "pharmaceutical carrier" is a pharmaceutically acceptable solvent, suspending agent or vehicle for delivering the anti-viral agent to the animal or human. The carrier may be liquid or solid and is selected with the planned manner of administration in mind.

As used herein, "anti-viral compounds" are the carbamic acid ester derivatives described above.

B. The Anti-Viral Compounds

Aryl carbamic acid ester has the following formula:

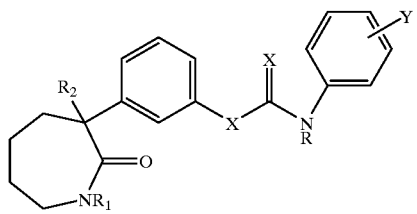

wherein X is independently oxygen or sulfur, R is selected from the group consisting of hydrogen and alkyl having from 1 to 4 carbon atoms, $R_1$ is selected from the group consisting of hydrogen and alkyl having from 1 to 4 carbon atoms, wherein $R_2$ is independently selected from the group consisting of hydrogen and alkyl having from 1 to 4 carbon atoms, and wherein Y is selected from the group consisting of hydrogen, chloro, fluoro, bromo, hydroxy, oxychloro and sulfhydryl or a pharmaceutical addition salts or prodrug thereof.

The preferred compound is (4-chlorophenyl)-carbamic acid, 3-(hexahydro-3-ethyl-1-methyl-2-oxo-1H-azepin-3-yl) 2 phenyl ester; wherein X is oxygen, Y is chloro, .R is hydrogen, $R_2$ is ethyl and $R_1$ is methyl. Its formula is:

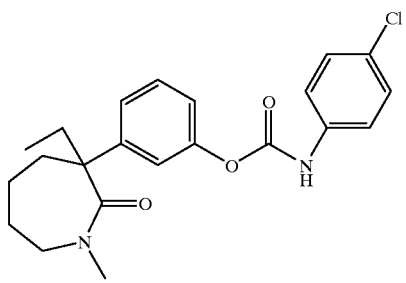

The pharmaceutically acceptable salts of the carbamic acid ester derivatives include the conventional non-toxic salts or the quaternary ammonium salts of the carbamic acid ester derivatives formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the carbamic acid ester derivatives which contain a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's *Pharmaceutical Sciences*, 17th ed., Mack Publishing Company, Easton, Pa., 1985, p. 1418, the disclosure of which is hereby incorporated by reference. The disclosures of all of the references cited herein are hereby incorporated herein by reference in their entirety.

C. Synthesis

The carbamic acid ester derivatives can be prepared in a number of ways well known to one skilled in the art of organic synthesis. The carbamic acid ester derivatives can be synthesized using the methods described below, together with synthetic methods known in the art of synthetic organic chemistry, or variations thereon as appreciated by those skilled in the art. Preferred methods include but are not limited to those methods described below. Relevant portions of each of the references cited below are hereby incorporated herein by reference.

The preferred compound, (4-chlorophenyl)-carbamic acid, 3-(hexahydro-3-ethyl-1-methyl-2-oxo-1H-azepin-3-yl) 2 phenyl ester, can be prepared as follows:

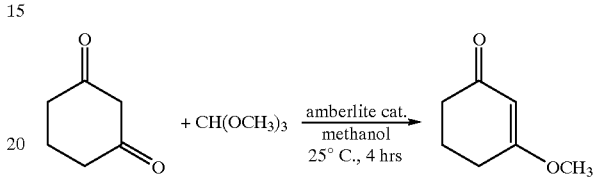

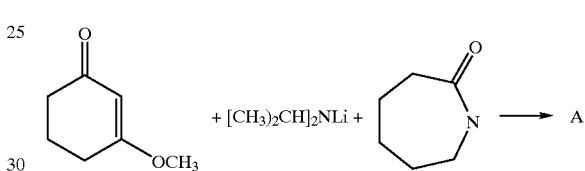

A in acetonitrile, lithium bromide, copper bromide at 25° C. for 16 hours yields B B+$[CH_3]_2CH]_2NLi$+$CH_3CH_2I$ in tetrahydrofuran at −10° Cm 15 min and then at 65° C. for six hours yields C.

A is

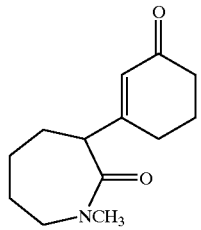

B is

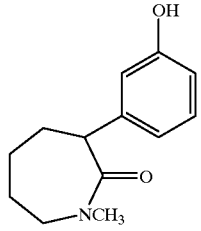

C is

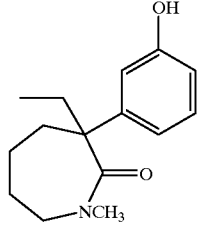

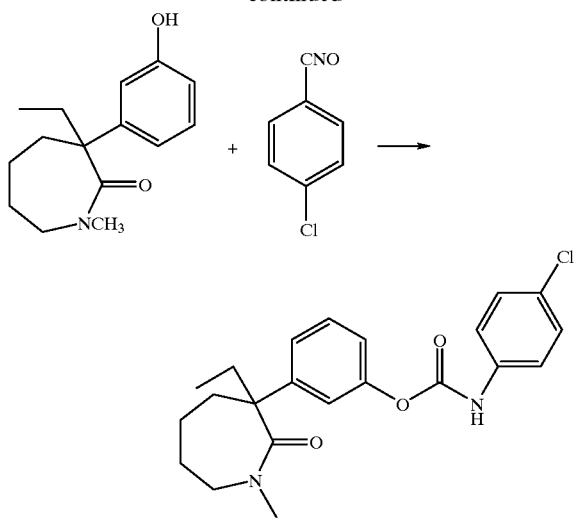

First 3-methoxycyclohexenone (see Shepherd, et al. *J. Chem Soc. Perkin Trans I*, 2153 (1987), for a synthetic method for making the 3-methxoycyclohexenone from 1,3-cyclohexanedione and trimethyl orthoformate) is reacted with N-methyl caprolactam in the presence of an organo-lithium compound, preferably lithium diisopropylamide, (see for example, U.S. Pat. No. 4,197,241). The resultant product is treated with lithium bromide and copper bromide in acteonitrile to convert the unsaturated ketone to the corresponding aromatic compound which is then reacted with ethyl iodide in the presence of a lithium catalyst (lithium diisopropylamide) to prepare the ethyl intermediate. The reaction with parachlorophenylisocyanate in pyridine using dibutyltin dilaurate as a catalyst results in 3-hexahydro-3-ethyl-1-methyl-2-oxo-1H-azepin-3-yl) phenyl ester of (4-chlorophenyl)-carbamic acid. Similar routes can be used to make the other derivatives or arylcarbamic acid esters of the type described herein.

D. Dosage and Dosage Delivery Forms

The compounds are generally safe. The compounds can be given orally, and as they are not very soluble, they are preferably given in tablet form or as a suspension orally or intraveneously.

Any suitable dosage can be given in the method of the invention. The type of compound and the carrier and the amount will vary widely depending on the species of the warm blooded animal or human, body weight, and virus being treated. The dosage administered will, of course, vary depending upon known factors, such as the pharmacodynamic characteristics of the particular agent and its mode and route of administration; the age, health and/or weight of the recipient; the nature and extent of the symptoms; the kind of concurrent treatment; the frequency of treatment; and the effect desired.

The carbamic acid ester is preferably micronized or powdered so that it is more easily dispersed and solubilized by the body. Processes for grinding or pulverizing drugs are well known in the art. For example, a hammer mill or similar milling device can be used. The preferred particle size is less than about $100\mu$ and preferably less than $50\mu$.

By way of general guidance, a dosage of as little as about 1 milligrams (mg) per kilogram (kg) of body weight and preferably as little as 10 mg/kg and up to about 10,000 mg per kg of body weight is suitable. Preferably from 10 mg/kg to about 5000 mg/kg of body weight is used. Most preferably the doses are between 250 mg/kg to about 5000 mg/kg.

Intravenously, the most preferred doses can range from about 1 to about 10 mg/kg/minute during a constant rate infusion. Aryl carbamic acid ester compounds can be administered in a single daily dose, or the total daily dosage can be administered in divided doses of two, three, or four times daily. The carbamic acid ester derivatives can be given in one or more doses on a daily basis and from one to three times a week. Twice weekly dosing over a period of at least several weeks is preferred and often the anti-viral compounds will be administered for extended periods of time and maybe for the lifetime of the patient.

The carbamic acid ester derivatives can also be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen.

Generally, the dosage in man is lower than for small warm blooded mammals such as mice. A dosage unit can comprise a single compound or mixtures thereof with other compounds or other viral inhibiting compounds. The dosage unit can also comprise diluents, extenders, carriers and the like. The unit can be in solid or gel form such as pills, tablets, capsules and the like or in liquid form suitable for oral, rectal, topical, intravenous injection or parenteral administration or injection into or around the virus.

The carbamic acid ester derivatives are typically mixed with a pharmaceutically acceptable carrier. This carrier can be a solid or liquid and the type is generally chosen based on the type of administration being used. The active agent can be coadministered in the form of a tablet or capsule, as an agglomerated powder or in a liquid form. Examples of suitable solid carriers include lactose, sucrose, gelatin and agar. Capsule or tablets can be easily formulated and can be made easy to swallow or chew; other solid forms include granules, and bulk powders. Tablets can contain suitable binders, lubricants, diluents, disintegrating agents, coloring agents, flavoring agents, flow-inducing agents, and melting agents. Examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms can contain, for example, suitable solvents, preservatives, emulsifying agents, suspending agents, diluents, sweeteners, thickeners, and melting agents. Oral dosage forms optionally contain flavorants and coloring agents. Parenteral and intravenous forms would also include minerals and other materials to make them compatible with the type of injection or delivery system chosen.

Examples of Formulation

The carbamic acid ester derivatives of this invention can be administered as treatment for viral infections by any means that produces contact of the active agent with the agent's site of action in the body. They can be administered by any conventional means available for use in conjunction with pharmaceuticals, either as individual therapeutic agents or in a combination of therapeutic agents. They can be administered alone, but generally administered with a pharmaceutical carrier selected on the basis of the chosen route of administration and standard pharmaceutical practice.

The carbamic acid ester can be administered in oral dosage forms as tablets, capsules (each of which includes sustained release or timed release formulations), pills, powders, granules, elixirs, tinctures, suspensions, syrups, and emulsions. The carbamic acid ester derivatives can also be administered in intravenous (bolus or infusion), intraperitoneal, subcutaneous, or intramuscular form, all using dosage forms well known to those of ordinary skill in the pharmaceutical arts.

In the methods of the present invention, the compounds herein described in detail can form the active ingredient, and are typically administered in admixture with suitable pharmaceutical diluents, excipients, or carriers (collectively referred to herein as a pharmaceutically acceptable carrier or carrier materials) suitably selected with respect to the intended form of administration, that is, oral tablets, capsules, elixirs, syrups and the like, and consistent with conventional pharmaceutical practices.

For instance, for oral administration in the dosage unit form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like. For oral administration in liquid dosage form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The carbamic acid ester derivatives can also be administered in the form of liposome delivery systems, such as small unilamellar vesicles, large unilamallar vesicles, and multilamellar vesicles. Liposomes can be formed from a variety of phospholipids, such as cholesterol, stearylamine, or phosphatidylcholines.

Carbamic acid esters can also be coupled with soluble polymers as targetable drug carriers. Such polymers can include polyvinylpyrrolidone, pyran copolymer, polyhydroxylpropylmethacrylamide-phenol, polyhydroxyethylaspartamidephenol, or polyethyleneoxide-polylysine substituted with palmitoyl residues. Furthermore, the compounds of the present invention can be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (compositions suitable for administration) contain from about 1 milligram to about 1000 milligrams of active ingredient per dosage unit. Preferably the dosage forms will contain from about 10 mg to about 500 mg. In these pharmaceutical compositions the active ingredient will ordinarily be present in an amount of about 0.5 to about 95% by weight based on the total weight of the dosage unit.

The active ingredient can be administered orally in solid dosage forms, such as capsules, tablets, and powders, or in liquid dosage forms, such as elixirs, syrups, and suspensions. It can also be administered parentally, in sterile liquid dosage forms, including liposomes.

Gelatin capsules can contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance. In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient or a liposome, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol. Suitable pharmaceutical carriers are described in *Remington's Pharmaceutical Sciences,* Mack Publishing Company, a standard reference text in this field.

Useful pharmaceutical dosage forms for administration of the compounds of this invention are illustrated as follows:

Capsules

A large number of unit capsules are prepared by filling standard two-piece hard gelatin capsules each with 100 milligrams of powdered active ingredient, 150 milligrams of lactose, 50 milligrams of cellulose, and 6 milligrams magnesium stearate.

Soft Gelatin Capsules

A mixture of active ingredient in a digestible oil such as soybean oil, cottonseed oil or olive oil is prepared and injected by means of a positive displacement pump into gelatin to form soft gelatin capsules containing 100 milligrams of the active ingredient. The capsules are washed and dried.

Tablets

A large number of tablets are prepared by conventional procedures so that the dosage unit was 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings can be applied to increase palatability or delay absorption.

Injectable

A parenteral composition suitable for administration by injection is prepared by stirring 1.5% by weight of active ingredient in 10% by volume propylene glycol and water. The solution is made isotonic with sodium chloride and sterilized.

Suspension

An aqueous suspension is prepared for oral administration so that each 5 ml contain 100 mg of finely divided active ingredient, 200 mg of sodium carboxymethyl cellulose, 5 mg of sodium benzoate, 1.0 g of sorbitol solution, U.S.P., and 0.025 ml of vanillin.

The present invention also includes pharmaceutical kits useful, for example, for the treatment of HIV infection, which comprise one or more containers containing a pharmaceutical composition comprising a therapeutically effective amount of a compound of formula (I). Such kits can further include, if desired, one or more of various conventional pharmaceutical kit components, such as, for example, containers with one or more pharmaceutically acceptable carriers, additional containers, etc., as will be readily apparent to those skilled in the art. Printed instructions, either as inserts or as labels, indicating quantities of the components to be administered, guidelines for administration, and/or guidelines for mixing the components, can also be included in the kit In the present disclosure it should be understood that the specified materials and conditions are important in practicing the invention but that unspecified materials and conditions are not excluded so long as they do not prevent the benefits of the invention from being realized.

F. Method of Treatment

The method of treatment can be any suitable method which is effective in the treatment of the particular virus. The above formulations can be used for treatment. Treatment can be oral, rectal, topical, parenteral or intravenous administration and the like. The method of administering an effective amount also varies depending on the virus being treated. It is believed that parenteral treatment by intravenous, subcutaneous, or intramuscular application of the aryl carbamate ester compounds, formulated with an appropriate carrier, additional viral inhibiting compound or compounds or diluent to facilitate application will be the preferred method of administering the compounds to warm blooded animals.

The actual time or length of treatment and dosage will depend on the virus being treated and the desired blood levels.

The carbamic acid ester derivatives can also be used as an anti-fungal treatment and administered as for the anti-viral treatment or also can be applied topically in a cream, gel or liquid form. They can also be prepared as a suppository.

G. Combination Therapy

One or more carbamic acid ester derivatives can be combined with other antiviral agents or potentiators. Potentiators are materials which affect the body's response to the anti-viral agent. In the case of HIV a combination therapy with AZT, TC-3 or protease inhibitors is effective. In the case of hepatitis, cyclovir, famciclovir or valacyclovir, Ribavirin, interferon or combinations of Ribavirin and Interferon or beta globulin is administered as a combination therapy. For herpes, a recombinant alpha interferon can be used.

In some embodiments, the aryl carbamate ester compound is used in combination with one or more potentiators and/or antiviral agents for the treatment of viral infections. An exemplary potentiator is triprolidine or its cis-isomer which are used in combination with chemotherapeutic agents and thearyl carbamate estercompound. Triprolidine is described in U.S. Pat. No. 5,114,951 (1992). Another potentiator is procodazole, 1H-Benzimidazole-2-propanoic acid; [β(2-benzimidazole) propionic acid; 2-(2-carboxyethyl) benzimidazole; propazol]. Procodazole is a non-specific immunoprotective agent active against viral and bacterial infections that is used with the compositions claimed herein. It is effective with the aryl carbamate ester compound in treating viral infections. Procodazole can also be combined with the carbamate ester compound and other antiviral agents. Other potentiators which can be used aryl carbamate ester compounds include monensin, an anti-sense inhibitor of the RAD51 gene, bromodeoxyuridine, dipyridamole, indomethacin, a monoclonal antibody, an anti-transferrin receptor immunotoxin, metoclopramide, 7-thia-8-oxoguanosine, N-solanesyl-N,N'-bis(3,4-dimethoxybenzyl) ethylenediamine, leucovorin, heparin, N-[4-[(4-fluorphenyl) sulfonly]phenyl] acetamide, heparin sulfate, cimetidine, a radiosensitizer, a chemosensitizer, a hypoxic cell cytotoxic agent, muramyl dipeptide, vitamin A, 2'-deoxycoformycin, a bis-diketopiperazine derivative, and dimethyl sulfoxide.

In some embodiments of the invention, an aryl carbamate estercompound is used in combination with one or more other therapeutic agents, such as anti-inflammatory, anti-viral, anti-fungal, amoebicidal, trichomonocidal, analgesic, anti-neoplastic, anti-hypertensives, anti-microbial and/or steroid drugs, to treat antiviral infections. In some preferred embodiments, patients with viral infections are treated with a combination of one or more aryl carbamate ester compounds with one or more of beta-lactam antibiotics, tetracyclines, chloramphenicol, neomycin, gramicidin, bacitracin, sulfonamides, nitrofurazone, nalidixic acid, cortisone, hydrocortisone, betamethasone, dexamethasone, fluocortolone, prednisolone, triamcinolone, indomethacin, sulindac, acyclovir, amantadine, rimantadine, recombinant soluble CD4 (rsCD4), anti-receptor antibodies (for rhinoviruses), nevirapine, cidofovir (Vistide™), trisodium phosphonoformate (Foscarnet™), famcyclovir, pencyclovir, valacyclovir, nucleic acid/replication inhibitors, interferon, zidovudine (AZT, Retrovir™), didanosine (dideoxyinosine, ddI, Videx™), stavudine (d4T, Zerit™), zalcitabine (dideoxycytosine, ddC, Hivid™), nevirapine (Viramune™), lamivudine (Epivir™, 3TC), protease inhibitors, saquinavir (Invirase™, Fortovase™), ritonavir (Norvir™), nelfinavir (Viracept™), efavirenz (Sustiva™), abacavir (Ziagen™), amprenavir (Agenerase™) indinavir (Crixivan™), ganciclovir, AzDU, delavirdine (Rescriptor™), rifampin, clathiromycin, erythropoietin, colony stimulating factors (G-CSF and GM-CSF), non-nucleoside reverse transcriptase inhibitors, nucleoside inhibitors, adriamycin, fluorouracil, methotrexate, asparaginase and combinations thereof.

The combination therapy can be sequential, that is the treatment with one agent first and then the second agent, or it can be treatment with both agents at the same time. The sequential therapy can be within a reasonable time after the completion of the first therapy before beginning the second therapy. The treatment with both agents at the same time can be in the same daily dose or in separate doses. For example treatment with one agent on day 1 and the other on day 2. The exact regimen will depend on the disease being treated, the severity of the infection and the response to the treatment.

Mechanism

The mechanism of action of the carbamic acid esters is not known. The preferred aryl carbamic acid ester did not show activity as a protease inhibitor when screened using a fluorometric method or as an integrase inhibitor. These results are summarized below:

Protease Inhibition Assay

Protease inhibition is evaluated using a fluorometric method. Enzyme (Bachem) is diluted to 116 μgm/ml in 50 mM NaOAC, 5 mM DTT, 2 mM EDTA, 10% glycerol (pH 5.0) and stored as 10 μl samples at −20° C., HIV protease substrates I (Molecular Probes) is diluted to a working concentration of 0.32 nmoles/μl. Enzyme (20 μl) and drug (20 μl) are added to each well of a microtiter plate as appropriate. Positive and negative control are evaluated in parallel. Fluorescence is quantitated on Labsystems Fluroskan II using 355 nm/460nm at 37° C. at time zero and at 30 minute intervals for 2 hours. In instances where autofluorescence precludes use of the fluorometric HIV-1 protease assay or confirmation of a result is required, an HPLC based protease assay can be employed.

Integrase Inhibition Assay

A biochemical integrase assay described by Craigie et at (HIV, vol. 2: *A practical Approach*) *Biochemistry, Molecular Biology and Drug Discovery* Ed. J. Karn 1995) to screen agents for their ability to inhibit HIV-1 integrase. In this system, a kinased oligonucleotide serves as the target of 3' processing and the subsequent strand transfer reaction. The 3' processing reaction involves the removal of 2 nucleotides from the 31 ends of the substrate and this is followed by the strand transfer reaction in which the 3' ends are joined to the exposed 5' ends. The 20 μl reaction mixture contains 25 mM MOPS (pH 7.2), 100 g/ ml BSA, 10 mM , β-mercaptoethanol, 10% glycerol, 7.5 mM MnCl$_2$, 25 nM (7 ng) substrate (Oligo's Etc., Wilsonville, Ore.) and 200 nM (128 ng) integrase (NIAID AIDS Research and Reference Reagent Program, Bethesda, Md.). The reaction proceeds at 37° C. for 1–2 hours and is terminated by the addition of 20 μl of sequencing stop solution (USB Amersham, Arlington Heights, Ill.). The reaction products are visualized by autoradiography following electrophoresis in 15% polyacrylamide 6M Urea gel. The substrate migrates as a 30 mer, the product of 3' processing migrates as an N-2 band and the strand transfer products migrate more slowly at various sizes larger than the substrate.

| Concentration (nM) | 0 | 1 | 10 | 100 | 1000 |
|---|---|---|---|---|---|
| sample 1 | 30.7 | 26.1 | 29.2 | 26.5 | 10.0 |
| sample 2 | 26.3 | 30.3 | 27.6 | 25.5 | 6.7 |
| mean | 28.5 | 28.2 | 28.4 | 26.0 | 8.3 |
| % no drug control | 100.0 | 99.0 | 99.7 | 91.3 | |

Protease Inhibition 3-hexahydro-3-ethyl- 1 -methyl-2-oxo- 1H-azepin-3-yl) phenyl ester of 4-chlorophenyl carbamic acid fluorometric units

| Concentration (nM) | 0 | 0.1 | 1 | 10 | 100 |
|---|---|---|---|---|---|
| sample 1 | 30.7 | 24.7 | 27.4 | 28.5 | 29.3 |
| sample 2 | 26.3 | 31.2 | 27.5 | 25.1 | 30.7 |
| mean | 28.5 | 27.9 | 27.4 | 26.8 | 30.0 |
| % ND control | 100.0 | 98.2 | 96.4 | 94.2 | 105.3 |

The EC$_{50}$ value is >100 μg/ml for (4-chlorophenyl)-carbamic acid, 3-(hexahydro-3-ethyl- 1-methyl-2-oxo-1H-azepin-3-yl) 2 phenyl ester and 0.699 μM/ml for 654021.

HIV-1 Integrase Inhibition (4-chlorophenyl)-carbamic acid, 3-(hexahydro-3-ethyl-1-methyl-2-oxo-1H-azepin-3-yl) 2 phenyl ester

| Concentration (μg/ml) | 0 | 0.1 | 1 | 10 | 100 |
|---|---|---|---|---|---|
| sample 1 | 9966 | 10151.6 | 9644.6 | 10964.5 | 9648.5 |
| sample 2 | 9149 | 9664.3 | 10505.5 | 1129.7 | 12235.7 |
| mean | 9558 | 9908 | 10075 | 10097 | 10942 |
| % no drug control | 100.0 | 103.7 | 105.4 | 116.1 | 114.5 |

The IC50 (μg/mml) is greater than 100 for this compound.

HIV-1 Integrase inhibition by 654021F A Control Drug

| Concentration (μg/ml) | 0 | 1 | 10 | 100 | 1000 |
|---|---|---|---|---|---|
| sample 1 | 30.7 | 26.1 | 29.2 | 26.5 | 10.0 |
| sample 2 | 26.3 | 30.3 | 27.6 | 25.5 | 6.7 |
| mean | 28.5 | 28.2 | 28.4 | 26.0 | 8.3 |
| % no drug control | 100.0 | 99.0 | 99.7 | 91.3 | 29.3 |

The IC 50 (nM) is 699.01

The compounds are generally safe. The LD$_{50}$ is fairly high and there are no special handling requirements. The compounds can be given orally, and as they are not very soluble, they are preferably given in tablet form or as a suspension or liposome.

Virus Preparation

A pretitered aliquot of virus is removed from the freezer (−80° C.) and allowed to thaw slowly to room temperature in a biological safety cabinet. The virus is resuspended and diluted into tissue culture medium such that the amount of virus added to each well in a volume of 50 μl will be the amount determined to give complete cell killing at 6 days post infection. In general, the virus pools produced with IIIB isolate of HIV required the addition of 5 μl of virus per well. Pools of RF virus were 5 to 10 fold more potent requiring 0.5–1 μl of virus per well. TCID$_{50}$ calculation by endpoint titration in CEM-SS cells indicated that the multiplicity of infection of these assays ranged from 0.005 to 2.5.

Plate Format

The format of the test plate has been standardized. Each plate contains cell control wells (cells only), virus control wells (cells plus virus), drug toxicity control wells (cells plus drug lonely), drug colorimetric control wells (drug only) as well as experimental wells (drug plus cells plus virus).

XTT Staining of Screening Plates

After 6 days (or the experimental period) of incubation at 37° C. in a 5% carbon dioxide incubator the test plates are analyzed by staining with the tetrazolium dye XTT. XTT-tetrazolium is metabolized by the mitochondrial enzymes of metabolically active cells to a soluble formazan product, allowing the rapid quantitative analysis of the inhibition of HIV-induced cell killing by anti-HIV test substances. On day 6 post-infection plates are removed from the incubator and observed. The use of round bottom microtiter plates allows rapid macroscopic analysis of the activity of a given test compound by the evaluation of pellet size. The results of the macroscopic observations were confirmed and enhanced by further microscopic analysis.

XTT solution is prepared daily as a stock of 1 mg/ml in PBS. Phenazine methosulfate (PMS) solution is prepared at 15 mg/ml in PBS and stored in the dark at −20° C. XTT/PMS stock is prepared immediately before use by diluting the PMS 1:100 into PBS and adding 40 µl per ml of XTT solution. Fifty microliters of XTT/PMS is added to each well of the plate and the plate is reincubated or 4 hours at 37° C. Adhesive plate sealers are used in place of the lids, the sealed plate is inverted several times to mix the soluble formazan product and the plate is read spectrophotometrically at 450 nm with a Molecular Devices Vmax plate reader. Percent cell reduction, percent cell viability, $IC_{25,50,\ \&\ 95}$ and $TC_{25,50,\ \&\ 95}$ can then be calculated.

Reverse Transcriptase Activity Analysis

A microtiter-based reveres transcriptase (RT) reaction is utilized (Buckheit et al (1991) *AIDS Research and Human Retroviruses* 7:295–302). Tritiated thymidine triphosphate (NEN)(TTP) is resuspended in distilled water at 5 Ci/ml. Poly rA and oligo dT are prepared as a stock solution which is kept at −20° C. The RT reaction buffer is prepared fresh on a daily basis and consists of 125 µl 1M EGTA, 125 µl water, 125 µl Triton X-100, 50 µl Tris (pH 7.4), 50 µl MDDT, and 40 µl 1M $MgCl_2$. These three solutions are mixed together in a ratio of 1 part TTP, 2.5 parts poly rA:oligo dT, 2.5 parts reaction buffer and 4 parts distilled water. Ten microliters of this reaction mixture is placed in a round bottom microtiter place and 15 µl of virus containing supernatant is added and mixed. The plate is incubated at 37° C. and incubated for 60 minutes. Following reaction, the reaction volume is spotted onto filter mats, washed 6 times for 5 minutes each in a 5% sodium phosphate buffer, 2 times for 1 minute each in distilled water, 2 times for 1 minute each in 70% ethanol, and then dried. The dried filter mat is placed in a plastic sample bag, Betaplate scintillation fluid is added and the bag is heat sealed. Incorporated radioactivity is quantified utilizing a Wallac Microbeta scintillation counter.

contains an integrated HIV genome or provirus. Chronically infected CEM, H9 and U937 cell lines have been prepared and cultured by Southern Research Institute, Frederick Md. and are available from them.

CEM-SS cells chronically infected with HIV isolate, for example SKI (CEM-SKI) are cultured in RPM1640 tissue culture medium supplemented with 10% fetal bovine serum and antibiotics. Selection is performed by culturing the cells in the presence of the compound to be tested in T25 flasks. CEM-SKI or other infected cells with no added drug are used as the control cells. Cells are allowed to grow to a density of approximately 1×106 cells/ml and are then passaged at a 1:10 dilution. After a period of time, usually one week intervals of drug treatment, cells are evaluated to determine if the inhibitory activity of the compound has been affected by treatment of the cells with either compounds. The drug concentration in the flask is then increased two-fold and the cells maintained as above.

The cell populations contain integrated copies of the HIV genome and constitutively produce HIV at relatively high levels or are latently infected and only produce virus after stimulation with phorbol esters, tumor necrosis factor or IL6(U1 and ACH2). Reductions in virus products were observed when quantifying supernatant reverse transcriptase activity, Toxicity Values are measured by XTT and activity of the compound in the tests is measured by a Reverse Transcriptase analysis.

EXAMPLE 1

HIV-1

A long tern in vitro study of 3-hexahydro-3-ethyl-1-methyl-2-oxo-1H-azepin-3-yl)phenyl ester of 4-chlorophenyl carbamic acid against an HIV-1 cell line, CEMSKI, was conducted at three different levels. The results with CEMSKI cells were reported at weekly intervals. The reverse trascriptase data is summarized below.

| CEMSKI cell line | | | | | | | | |
|---|---|---|---|---|---|---|---|---|
| Day | 4 | 11 | 18 | 25 | 32 | 39 | 46 | 53 |
| No Drug | 8942 | 6976 | 9810 | 7139 | 4628 | 6976 | 4749 | 5774 |
| 7 µg/ml | 8474 | 7217 | 9141 | 7247 | 3145 | 7216 | 4216 | 5516 |
| 15 µg/ml | 6261 | 5914 | 8799 | 6071 | 2329 | 5914 | 4705 | 4552 |
| 30 µg/ml | 1265 | 2605 | 4959 | 2724 | 1234 | 2607 | 2261 | 1699 |
| Day | 60 | 67 | 74 | 71 | 88 | 95 | 102 | 109 |
| No Drug | 5271 | 6241 | 10047 | 9520 | 4271 | 14675 | 13339 | 85558 |
| 7 µg/ml | 4962 | 6437 | 9516 | 10004 | 4138 | 12844 | 13339 | 64067 |
| 15 µg/ml | 5012 | 5839 | 6701 | 7510 | 3965 | 11186 | 12252 | 56462 |
| 30 µg/ml | 1968 | 2522 | 3293 | 2954 | 2579 | 7623 | 3671 | 24800 |

Acute infection of most established human cell lines with HIV- I results in the eventual establishment of a constitutive virus-producing chronically infected cell line. The cells can be passaged for long periods of time in culture without loss of virus production. These cells may be utilized to evaluate the effects of anti-HIV compounds on syncytium formation or to evaluate the effects of anti-HIV compounds on levels of virus production from these cells. Chronically infected cell lines exhibit little or no cell surface CD4 and cannot be super-infected with other isolates of HIV-1. Each of the cells This test was run through 222 days and the data remained consistent.

The CEMSKI cell line is a viral strain of the CEMSS cell line.

EXAMPLE 3

CEMRF

A long term in vitro study of 3-hexahydro-3-ethyl-1-methyl-2-oxo-1H-azepin-3-yl)phenyl ester of 4-chlorophenyl carbamic acid against an HIV-1 cell line, CEMRF, was conducted at three different levels. The results with CEMRF cells were reported at weekly intervals. The reverse transcriptase data is summarized below. CEMRF is a chronic HIV cell line.

| Day | 4 | 11 | 18 | 25 | 32 | 39 | 46 | 53 |
|---|---|---|---|---|---|---|---|---|
| No Drug | 2001 | 1561 | 1624 | 1723 | 1361 | 1245 | 1610 | 1394 |
| 7 µg/ml | 1942 | 1537 | 1683 | 1624 | 1286 | 1368 | 1588 | 1482 |
| 15 µg/ml | 1402 | 1402 | 1281 | 1582 | 1140 | 1028 | 1056 | 1160 |
| 30 µg/ml | 650 | 463 | 221 | 643 | 462 | 221 | 149 | 281 |

| Day | 60 | 67 | 74 | 71 | 88 | 95 | 102 | 109 |
|---|---|---|---|---|---|---|---|---|
| No Drug | 1409 | 1297 | 1610 | 1564 | 1522 | 1462 | 1448 | 1642 |
| 7 µg/ml | 1381 | 1231 | 1528 | 1321 | 1454 | 1168 | 1463 | 1440 |
| 15 µg/ml | 1056 | 1002 | 1201 | 1108 | 1068 | 1004 | 1165 | 1265 |
| 30 µg/ml | 248 | 147 | 161 | 201 | 249 | 176 | 197 | 370 |

This test was run through 222 days and the data remained consistent.

EXAMPLE 4

CEMIIIB

A long term in vitro study of 3-hexahydro-3-ethyl-1-methyl-2-oxo-1H-azepin-3-yl)phenyl ester of 4-chlorophenyl carbamic acid against an HIV-1 cell line, CEMIIIB was conducted at three different levels. The results with CEIIIB cells were reported at weekly intervals. The reverse transcriptase data is summarized below. The CEMIIIB is a viral strain of the CEMSS cell line and is a chronic HIV cell line.

| Day | 4 | 11 | 18 | 25 | 32 | 39 | 46 | 53 |
|---|---|---|---|---|---|---|---|---|
| No Drug | 1687 | 1333 | 1482 | 1883 | 1333 | 1482 | 1763 | 1321 |
| 7 µg/ml | 1643 | 1294 | 1521 | 1725 | 1239 | 1341 | 1694 | 1287 |
| 15 µg/ml | 1526 | 1168 | 1241 | 1361 | 1168 | 1162 | 1084 | 902 |
| 30 µg/ml | 602 | 265 | 581 | 496 | 268 | 381 | 562 | 308 |

| Day | 60 | 67 | 74 | 71 | 88 | 95 | 102 | 109 |
|---|---|---|---|---|---|---|---|---|
| No Drug | 16893 | 1165 | 1442 | 1408 | 8845 | 6733 | 9202 | 63253 |
| 7 µg/ml | 1631 | 1245 | 1502 | 1483 | 7383 | 5512 | 8512 | 58104 |
| 15 µg/ml | 1310 | 1093 | 763 | 1056 | 4415 | 3205 | 6902 | 60170 |
| 30 µg/ml | 241 | 301 | 202 | 321 | 370 | 299 | 928 | 2019 |

This test was run through 22 days and the data remained consistent.

EXAMPLE 5

CEMROD

A long term in vitro study of 3-hexahydro-3-ethyl-1-methyl-2-oxo-1H-azepin-3-yl)phenyl ester of 4-chlorophenyl carbamic acid against an HIV-2 cell line, CEMROD was conducted at three different levels. The results with CEMROD cells were reported at weekly intervals. The reverse transcriptase data showed similar decreases as those in the previous experiments.

EXAMPLE 6

U937IIIB

A long term in vitro study of 3-hexahydro-3-ethyl-1-methyl-2-oxo-1H-azepin-3-yl)phenyl ester of 4-chlorophenyl carbamic acid against an HIV-1 cell line, U937IIIB was conducted at three different levels. The results with U937IIIB cells were reported at weekly intervals. The reverse transcriptase data was similar to the data reported above.

EXAMPLE 7

U937RF

A long term in vitro study of 3-hexahydro-3-ethyl-1-methyl-2-oxo-1H-azepin-3-yl)phenyl ester of 4-chlorophenyl carbamic acid against U937RF, a protease resistant strain, was conducted at three different levels. The results with U937RF cells were reported at weekly intervals. The reverse transcriptase data is similar to that reported above Similar results are obtained with U937KN1272, a protease resistant strain.

What is claimed is:

1. A pharmaceutical composition comprising a safe and effective amount of a carbamic acid ester having the formula:

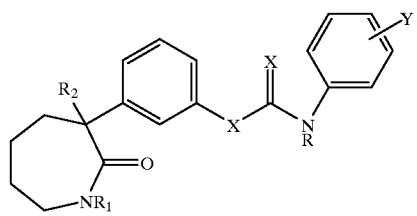

wherein X is independently oxygen or sulfur, R is selected from the group consisting of hydrogen and alkyl having from 1 to 4 carbon atoms, $R_1$ is selected from the group consisting of hydrogen and alkyl having from 1 to 4 carbon atoms, $R_2$ is independently selected from the group consisting of hydrogen and alkyl having from 1 to 4 carbon atoms, and Y is selected from the group consisting of hydrogen, chloro, fluoro, bromo, hydroxy, oxychloro and sulfhydryl or a pharmaceutical addition salt.

2. A pharmaceutical composition according to claim 1 comprising a pharmaceutically acceptable carrier and from about 1 mg to about 6000 mg of said carbamic acid ester or said pharmaceutical addition salt thereof.

3. A pharmaceutical composition according to claim 2 wherein said pharmaceutical addition salt is selected from the group consisting of chlorides, bromide, sulfate, nitrates, phosphate, sulfonate, formate, tartrate, maleate, malate, citrate, benzoate, salicylate, ascorbate and mixtures thereof.

4. A pharmaceutical composition according to claim 3 comprising from about 1500 mg to about 5000 mg of said carbamic acid ester.

5. A unit dosage composition comprising a safe and effective amount of a carbamic acid ester of the formula:

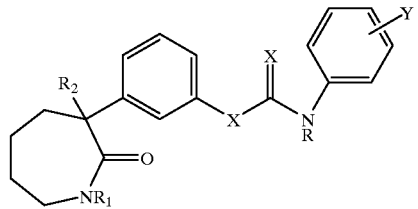

wherein X is independently oxygen or sulfur, R is selected from the group consisting of hydrogen and alkyl having from 1 to 4 carbon atoms, $R_1$ is selected from the group consisting of hydrogen and alkyl having from 1 to 4 carbon atoms, $R_2$ is independently selected from the group consisting of hydrogen and alkyl having from 1 to 4 carbon atoms, and Y is selected from the group consisting of hydrogen, chloro, fluoro, bromo, hydroxy, oxychloro and sulfhydryl or a pharmaceutical addition salt.

6. A unit dosage composition according to claim 5 comprising from about 1 mg to about 10.000 mg of said carbamic acid ester having the formula:

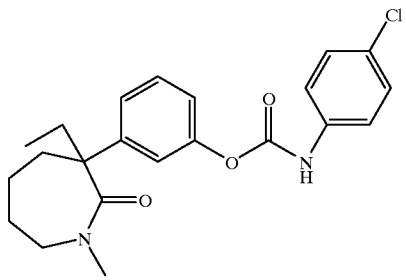

or said pharmaceutical addition salt thereof.

7. A unit dosage composition according to claim 6 wherein said pharmaceutical acceptable acid addition salt is selected from the group consisting of chloride, bromide, sulfate, nitrate, phosphate, sulfonate, formate, tartrate, maleate, malate, citrate, benzoate, salicylate, ascorbate and mixtures thereof.

8. A unit dosage composition according to claim 7 which is in a solid form comprising a carrier selected from the group consisting of lactose, sucrose, gelatin and agar and wherein said composition comprises from about 150 mg to about 4500 mg of said carbamic acid ester.

9. A unit dosage composition according to claim 7 in a liquid dosage form wherein said liquid dosage form is selected from the group consisting of aqueous solutions, emulsions, suspension solutions, and suspensions reconstituted from non-effervescent or effervescent preparations and wherein said composition comprises from about 1 mg to about 1000 mg of said carbamic acid ester.

10. A method of treating a viral infection comprising administering to a patient in need thereof a safe and effective amount of carbamic acid ester having the formula:

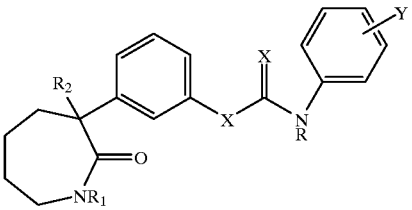

wherein X is independently oxygen or sulfur, R is selected from the group consisting of hydrogen and alkyl having from 1 to 4 carbon atoms, $R_1$ is selected from the group consisting of hydrogen and alkyl having from 1 to 4 carbon atoms, $R_2$ is independently selected from the group consisting of hydrogen and alkyl having from 1 to 4 carbon atoms, and Y is selected from the group consisting of hydrogen, chloro, fluoro, bromo, hydroxy, oxychloro and sulfhydryl or a pharmaceutical addition salt.

11. A method of treating a viral infection according to claim 10 wherein the viral infection is selected from the group consisting of HIV virus, influenza, hepatitis, herpes simplex and rhinovirus infection.

12. A method of treating HIV comprising administering to a patient in need thereof a safe and effective amount of a pharmaceutical composition comprising a carbamic acid ester having the formula:

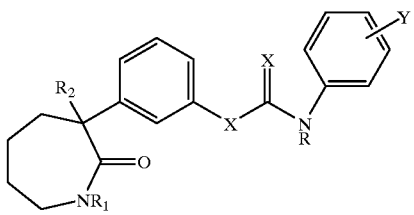

wherein X is independently oxygen or sulfur, R is selected from the group consisting of hydrogen and alkyl having from 1 to 4 carbon atoms, $R_1$ is selected from the group consisting of hydrogen and alkyl having from 1 to 4 carbon atoms, $R_2$ is independently selected from the group consisting of hydrogen and alkyl having from 1 to 4 carbon atoms, and Y is selected from the group consisting of hydrogen, chloro, fluoro, bromo, hydroxy, oxychloro and sulfhydryl or a pharmaceutical addition salt.

13. A method according to claim 12 wherein said pharmaceutical composition comprises from about 1 mg to about 6000 mg of said carbamic acid ester.

14. A method according to claim 12 wherein said pharmaceutical composition further comprises a member selected from the group consisting of AZT, TC-3 and protease inhibitors.

15. A method according to claim 12 wherein said carbamic acid ester is administered in a solid form and wherein said solid form includes a carrier selected from the group consisting of lactose, sucrose, gelatin and agar.

16. A method according to claim 12 wherein from about 250 mg/kg body weight to about 5000 mg/kg body weight of said carbamic acid ester is administered.

17. A method according to claim 12 wherein said carbamic acid ester is administered in a liquid dosage form and wherein said liquid dosage form is selected from the group consisting of aqueous solutions, alcohol solutions, emulsions, suspensions, and suspensions reconstituted from non-effervescent or effervescent preparations and suspensions in a pharmaceutically acceptable fat or oil.

18. A pharmaceutical composition according to claim 1 wherein said carbamic acid ester is in the form of a prodrug.

19. A pharmaceutical composition according to claim 1 wherein said carbamic acid ester is micronized.

20. A pharmaceutical composition according to claim 1 wherein said carbamic acid ester has the formula:

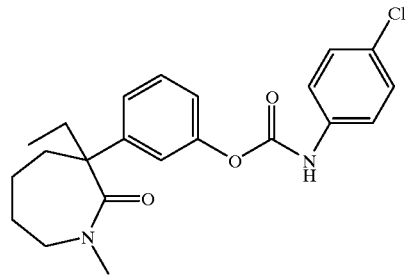

or said pharmaceutical addition salt thereof.

21. A unit dosage composition according to claim 5 wherein said carbamic acid ester is in the form of a prodrug.

22. A unit dosage composition according to claim 5 wherein said carbamic acid ester is micronized.

23. A unit dosage composition according to claim 5 further comprising a carrier, wherein said carrier is a liposome.

24. A unit dosage composition according to claim 5 wherein said pharmaceutical addition salt is a chloride.

25. A unit dosage composition according to claim 5 wherein said carbamic acid ester has the formula:

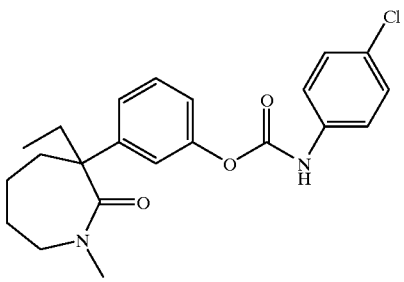

or said pharmaceutical addition salt thereof.

26. A method according to claim 10 wherein said carbamic acid ester is in the form of a prodrug.

27. A method according to claim 10 wherein said carbamic acid ester is micronized.

28. A method according to claim 10 wherein said carbamic acid ester has the formula:

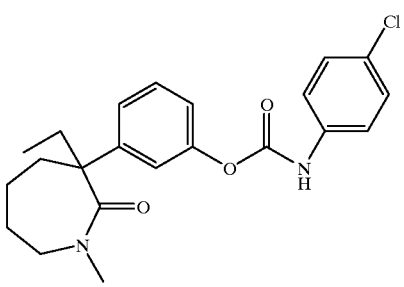

or said pharmaceutical addition salt thereof.

29. A method according to claim 12 wherein said carbamic acid ester has the formula:

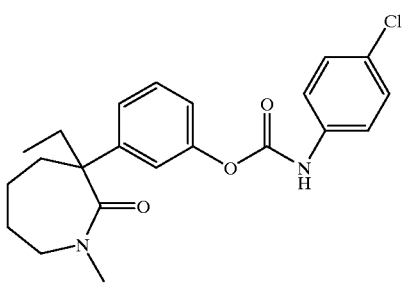

or said pharmaceutical addition salt thereof.

30. A pharmaceutical kit comprising:
a pharmaceutically acceptable carrier,
a safe and effective amount of a carbamic acid ester having the formula:

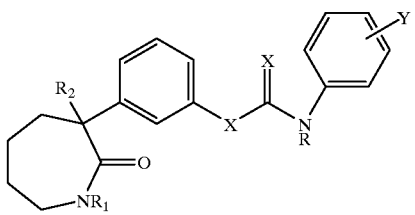

wherein X is independently oxygen or sulfur, R is selected from the group consisting of hydrogen and alkyl having from 1 to 4 carbon atoms, $R_1$ is selected from the group consisting of hydrogen and alkyl having from 1 to 4 carbon atoms, $R_2$ is independently selected from the group consisting of hydrogen and alkyl having from 1 to 4 carbon atoms, and Y is selected from the group consisting of hydrogen, chloro, fluoro, bromo, hydroxy, oxychloro and sulfhydryl or a pharmaceutical addition salt, and instructions for use in the treatment of a viral infection.

31. A kit according to claim 30 wherein said carbamic acid ester is in the form of a prodrug.

32. A kit according to claim 30 wherein said carbamic acid ester is micronized.

33. A kit according to claim 30 wherein said carbamic acid ester has the formula:

or said pharmaceutical addition salt thereof.

34. A method according to claim 10 wherein said viral infection is a retroviral infection.

35. A method according to claim 11 wherein said viral infection is a hepatitis C infection.

36. A method according to claim 10 wherein said viral infection is a Kaposi's sarcoma viral infection.

37. A pharmaceutical composition according to claim 1 further comprising a potentiator.

38. A unit dosage according to claim 5 further comprising a potentiator.

39. A unit dosage according to claim 38 further comprising a chemotherapeutic agent.

40. A method according to claim 10 further comprising a potentiator.

41. A method according to claim 40 further comprising a chemotherapeutic agent.

42. A pharmaceutical kit according to claim 30 further comprising a potentiator.

43. A pharmaceutical kit according to claim 42 further comprising a chemotherapeutic agent.

* * * * *

UNITED STATES PATENT AND TRADEMARK OFFICE
CERTIFICATE OF CORRECTION

PATENT NO.    : 6,225,307 B1                                              Page 1 of 1
DATED         : May 1, 2001
INVENTOR(S)   : Camden et al.

It is certified that error appears in the above-identified patent and that said Letters Patent is hereby corrected as shown below:

Column 18,
Lines 39-40, delete "sulfhydryl or a pharmaceutical addition salt" and insert in lieu thereof -- sulfhydryl; or a pharmaceutical addition salt thereof --.

Column 19,
Lines 6-7 and 62-63, delete "sulfhydryl or a pharmaceutical addition salt" and insert in lieu thereof -- sulfhydryl; or a pharmaceutical addition salt thereof --.
Line 9, delete "10.000" and insert in lieu thereof -- 10,000 --.

Column 20,
Lines 22-23, delete "sulfhydryl or a pharmaceutical addition salt" and insert in lieu thereof -- sulfhydryl; or a pharmaceutical addition salt thereof --.

Column 22,
Lines 19-20, delete "sulfhydryl or a pharmaceutical addition salt, and" and insert in lieu thereof -- sulfhydryl; or a pharmaceutical addition salt thereof; and --.

Signed and Sealed this

Twenty-seventh Day of May, 2003

JAMES E. ROGAN
*Director of the United States Patent and Trademark Office*